Figure 1:
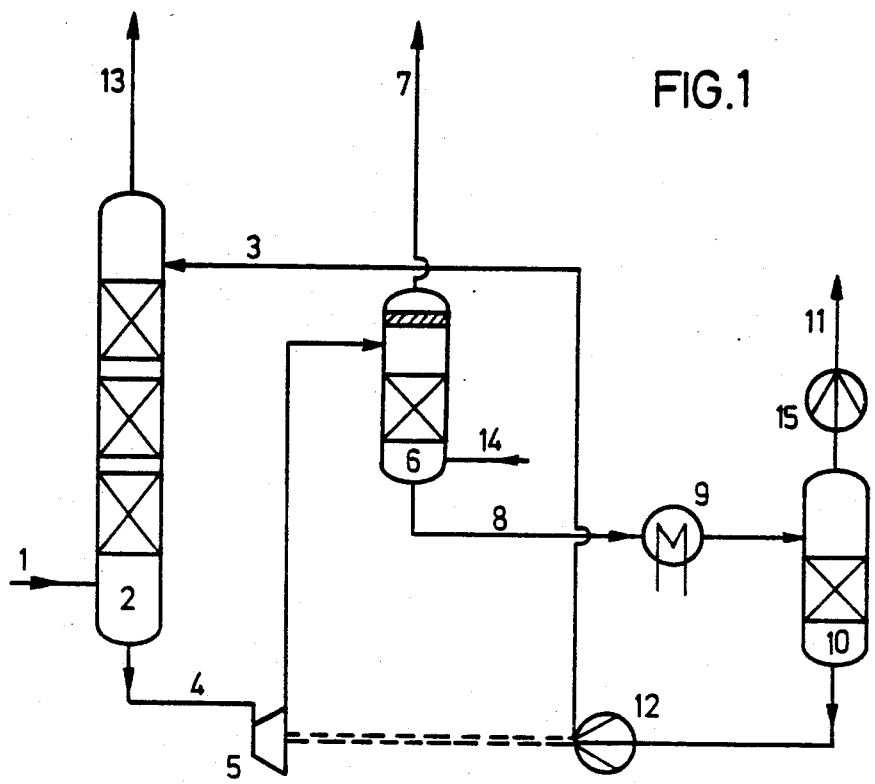

United States Patent [19]

Wagner et al.

[11] Patent Number: 4,551,158
[45] Date of Patent: Nov. 5, 1985

[54] REMOVAL OF $CO_2$ AND/OR $H_2S$ FROM GASES

[75] Inventors: Eckhart Wagner, Ludwigshafen; Klaus Volkamer, Frankenthal; Werner Hefner, Lampertheim; Ulrich Wagner, Limburgerhof, all of Fed. Rep. of Germany

[73] Assignee: BASF Aktiengesellschaft, Fed. Rep. of Germany

[21] Appl. No.: 584,867

[22] Filed: Feb. 29, 1984

[30] Foreign Application Priority Data

Mar. 8, 1983 [DE] Fed. Rep. of Germany ....... 3308088

[51] Int. Cl.$^4$ .............................. B01D 47/00
[52] U.S. Cl. ................................ 55/46; 55/55; 55/68; 55/73; 423/228
[58] Field of Search .............. 55/38, 40, 46, 48, 51, 55/68, 73, 55; 423/228, 229

[56] References Cited

U.S. PATENT DOCUMENTS

| | | | |
|---|---|---|---|
| 4,035,166 | 7/1977 | van Hecke | 55/38 |
| 4,080,424 | 3/1978 | Miller et al. | 55/68 X |
| 4,100,257 | 7/1978 | Sartori et al. | 55/73 X |
| 4,330,305 | 5/1982 | Kuessner et al. | 55/48 |
| 4,452,763 | 6/1984 | Van de Kraats et al. | 423/228 |

OTHER PUBLICATIONS

A. L. Kohl–F. C. Riesenfeld, Gas Purification, 3rd Edition, 1979.

Primary Examiner—Charles Hart
Attorney, Agent, or Firm—Keil & Weinkauf

[57] ABSTRACT $CO_2$ and/or $H_2S$ are removed from gases which contain $CO_2$ and/or $H_2S$ by means of an aqueous absorption liquid containing an alkanolamine, by a process wherein the said gas is treated, in an absorption stage, at from 40° to 100° C., with an aqueous absorption liquid containing from 20 to 70% by weight of methyldiethanolamine, the treated gas is taken off at the top of the absorption stage, the aqueous absorption liquid laden with $CO_2$ and/or $H_2S$ is taken off at the bottom of this stage and is regenerated by being let down in two or more flash stages, and the final flash stage is operated under reduced pressure and the regenerated absorption liquid is recycled to the absorption stage.

4 Claims, 2 Drawing Figures

REMOVAL OF CO₂ AND/OR H₂S FROM GASES

The present invention relates to a process for removing $CO_2$ and/or $H_2S$ from gases by means of an aqueous absorption liquid.

It has been disclosed, for example in A. L. Kohl-F. C. Riesenfeld, Gas Purification, 3rd Edition, 1979, that aqueous solutions of monoethanolamine or diethanolamine or a mixture of cyclotetramethylene sulfone and an aqueous solution of diisopropanolamine can be used as solvents for removing $CO_2$ and/or $H_2S$ from gases. In these processes, the solvent laden with $CO_2$ and, where relevant, $H_2S$ has to be regenerated in a stripping column by feeding in steam; this requires a substantial amount of energy. The use of a mixture of cyclotetramethylene sulfone and an aqueous solution of diisopropanolamine to remove $CO_2$ and, where relevant, $H_2S$ from natural gases containing higher hydrocarbons entails the additional disadvantages that the higher hydrocarbons have a relatively high solubility in this solvent, so that the acid gas taken off at the top of the stripping column has a relatively high content of hydrocarbons; if the acid gas contains $H_2S$, this hydrocarbon content can lead to difficulties in a downstream Claus unit. Moreover, primary or secondary alkanolamines, such as monoethanolamine or diethanolamine, can as a rule be used only as aqueous solutions having a relatively low concentration of these alkanolamines, since the use of higher concentrations may result in severe corrosion damage to plant components.

It is an object of the present invention to provide a process for removing $CO_2$ and/or $H_2S$ from gases containing $CO_2$ and/or $H_2S$ by means of an aqueous absorption liquid containing an alkanolamine, in which the removal of the stated substances can be effected using a substantially smaller amount of energy.

We have found that this and other objects and advantages are achieved, in accordance with the invention, by a process for removing $CO_2$ and/or $H_2S$ from a gas containing $CO_2$ and/or $H_2S$ by means of an aqueous absorption liquid containing an alkanolamine, wherein the said gas is treated, in an absorption stage, at from 40° to 100° C., with an aqueous absorption liquid containing from 20 to 70% by weight of methyldiethanolamine, the treated gas is taken off at the top of the absorption stage, the aqueous absorption liquid laden with $CO_2$ and/or $H_2S$ is taken off at the bottom of this stage and is regenerated by being let down in two or more flash stages, and the final flash stage is operated under reduced pressure and the regenerated absorption liquid is recycled to the absorption stage.

In an advantageous embodiment of the process, the water losses resulting from removal of water in the gas streams taken off at the top of the absorption stage and of the flash stages are compensated by feeding in, at the bottom of the penultimate flash stage, an amount of steam corresponding to the water loss.

In the novel process, the solvent laden with $CO_2$ and/or $H_2S$ is regenerated solely by flashing, without the use of a stripping column, so that a substantial reduction in both capital costs and energy costs is achieved. Furthermore, the novel process permits the use of a relatively high concentration of methyldiethanolamine in the absorption liquid, without corrosion damage to the gas washer taking place. Another advantage of the process is that water losses which occur in gas washers as a result of water being removed in the gas stream taken off at the top of the absorption column and of the flash chambers can be compensated by feeding in, at the bottom of the penultimate flash stage, an amount of steam corresponding to the water loss. Using this procedure, it is possible to regulate not only the water balance of the gas washer but also its heat balance, so that any heat exchanger present in the gas washer for regulating the heat balance can be smaller or, if appropriate, can be omitted. Operating the final flash stage under reduced pressure gives a regenerated absorption liquid which has a relatively low $CO_2$ and/or $H_2S$ content, so that smaller amounts of absorption liquid have to be circulated; this results in a corresponding saving of energy.

In another preferred embodiment of the process, the reduced pressure in the final flash stage is produced by means of a steam-jet ejector. It may be advantageous if the gas taken off at the top of the final flash stage is fed in, together with the steam used to operate the steam-jet ejector, at the bottom of the penultimate flash stage.

Examples of gases which can be treated using the novel process are coal gasification gases, synthesis gases, coke oven gases and, preferably, natural gases. The process is advantageously used for removing $CO_2$ and/or $H_2S$ from natural gases which contain higher hydrocarbons in addition to methane. These higher hydrocarbons are in general $C_2$–$C_{30}$-hydrocarbons, preferably $C_2$–$C_{20}$-hydrocarbons, in particular, $C_2$–$C_{12}$-hydrocarbons, which as a rule are aliphatic, eg. ethane, propane, isobutane, n-butane, isopentane, n-pentane, the hexanes, heptanes, octanes, nonanes and decanes and the higher homologs. The higher hydrocarbons can contain, in addition to the aliphatic hydrocarbons, aromatic hydrocarbons such as benzene. In general, the natural gases contain from 0.1 to 40, preferably from 0.5 to 30, in particular from 1 to 20, mole % of the higher hydrocarbons.

The gases contain in general from 1 to 90, preferably from 2 to 90, in particular from 5 to 60, mole % of $CO_2$. They can also contain $H_2S$ as a further acid gas, or can contain $H_2S$ alone, for example in an amount of from a few mole ppm, for example 1 mole ppm, to 50 mole %, preferably from 10 mole ppm to 40 mole %.

The solvent used for the novel process is an aqueous absorption liquid containing from 20 to 70, preferably from 30 to 65, in particular from 40 to 60, % by weight of methyldiethanolamine. Advantageously, an aqueous methyldiethanolamine solution is employed, for example an aqueous solution of technical-grade methyldiethanolamine. In an advantageous embodiment of the process, the aqueous methyldiethanolamine solution used additionally contains from 0.1 to 1, preferably from 0.2 to 0.8, in particular from 0.25 to 0.6, mole/liter of a primary amine or alkanolamine, such as monoethanolamine, preferably a secondary amine or alkanolamine, advantageously methylmonoethanolamine, and very particularly advantageously piperazine. The novel process is carried out as follows: the gas containing $CO_2$ and/or $H_2S$ is first treated, in an absorption stage, with the methyldiethanolamine-containing absorption liquid at from 40° to 100° C., preferably from 50° to 90° C., in particular from 60° to 80° C. The pressure in the absorption stage is in general from 10 to 110, preferably from 20 to 100, in particular from 30 to 90, bar. The absorption stage is advantageously an absorption column, in general a packed column or a column equipped with trays. Advantageously, the gas to be treated is fed in at the bottom and the absorption liquid is fed in at the top of the absorption column, the acid gases $CO_2$ and/or $H_2S$ being washed out by a counter-current procedure. While any $H_2S$ present is advantageously washed out to a substantial extent, in general so that the treated gas has an $H_2S$ content of not more than 120, preferably not more than 10, in particular not more than 3, mole ppm, it may be advantageous to wash out the $CO_2$ from the gas so that the treated gas contains not more than about 0.5–6, preferably from 0.5 to 5, in particular from 1 to 4, mole % of $CO_2$. The treated gas is advantageously taken off at the top of the absorption stage, expediently at a point above the feed of the absorption liquid. The absorption liquid laden with the acid gases $CO_2$ and/or $H_2S$ is advantageously taken off at the bottom of the absorption zone.

The laden absorption liquid is then regenerated in not less than 2, advantageously from 2 to 5, preferably 2 or 3, flash stages, the final flash stage being operated under reduced pressure and at the same time, if necessary, water losses due to the removal of water in the gas streams taken off at the top of the absorption stage and of the flash stages are compensated by feeding in, at the bottom of the penultimate flash stage, an amount of steam corresponding to the water loss. Preferably, a pressure of from 0.5 to about 1, preferably from 0.7 to about 1, bar is maintained in the final flash stage. In this flash stage, the reduced pressure can be obtained by means of, for example, an apparatus conventionally used for producing reduced pressure, eg. a vacuum pump, but particularly advantageously by means of a steam-jet ejector.

To compensate for water losses which arise in the process as a result of water being removed in the gas streams taken off at the top of the absorption stage and of the flash stages, an amount of steam corresponding to the water loss is advantageously fed in at the bottom of the penultimate flash stage. As a rule, the water present in the gas streams taken off is essentially removed in the form of steam. Low-pressure, medium-pressure or high-pressure steam, eg. steam under 1.5–100 bar, can be fed to the bottom of the penultimate flash stage. Preferably, low-pressure steam, eg. steam under 1.5–10, advantageously 1.5–5, bar, is used, since this steam is in general cheaply available.

The gas taken off at the top of the final flash stage can be released to the atmosphere or, if it still contains $H_2S$, can be worked up by oxidizing the $H_2S$, for example in a Claus unit. In an advantageous embodiment of the process, the reduced pressure in the final flash stage is obtained using a steam-jet ejector and, expediently, the gas taken off at the top of this stage is fed in, together with the steam used to operate the steam-jet ejector, at the bottom of the penultimate flash stage.

Where the steam used to operate the steam-jet ejector is fed in at the bottom of the penultimate flash stage, the ejector is advantageously operated using an amount of steam corresponding to that required to compensate the water losses in the process. However, it is also possible to operate the steam-jet ejector with an amount of steam smaller than that required to compensate the water losses, and in addition to feed in the lacking amount of steam at the bottom of the penultimate flash stage. The steam-jet ejector can be operated using medium-pressure or high-pressure steam. Medium-pressure steam, eg. under 5–20, preferably 5–10, bar, is preferably used.

The penultimate flash stage is advantageously operated under a pressure of about 1–5, preferably 1–2.5, in particular 1–1.5, bar.

Flashing is advantageously carried out using flash chambers which can, for example, also be in the form of columns. These flash chambers need not contain special baffles. However, it is also possible to use columns equipped with baffles, eg. packed columns.

The acid gases $CO_2$ and/or $H_2S$ are advantageously taken off at the top of the final flash stage or (where the gas taken off at the top of this stage is fed in, together with the steam for operating the steam-jet ejector, at the bottom of the penultimate flash stage) at the top of the penultimate flash stage. The regenerated absorption liquid taken off at the bottom of the final flash stage is recycled to the absorption stage.

Figure 2:
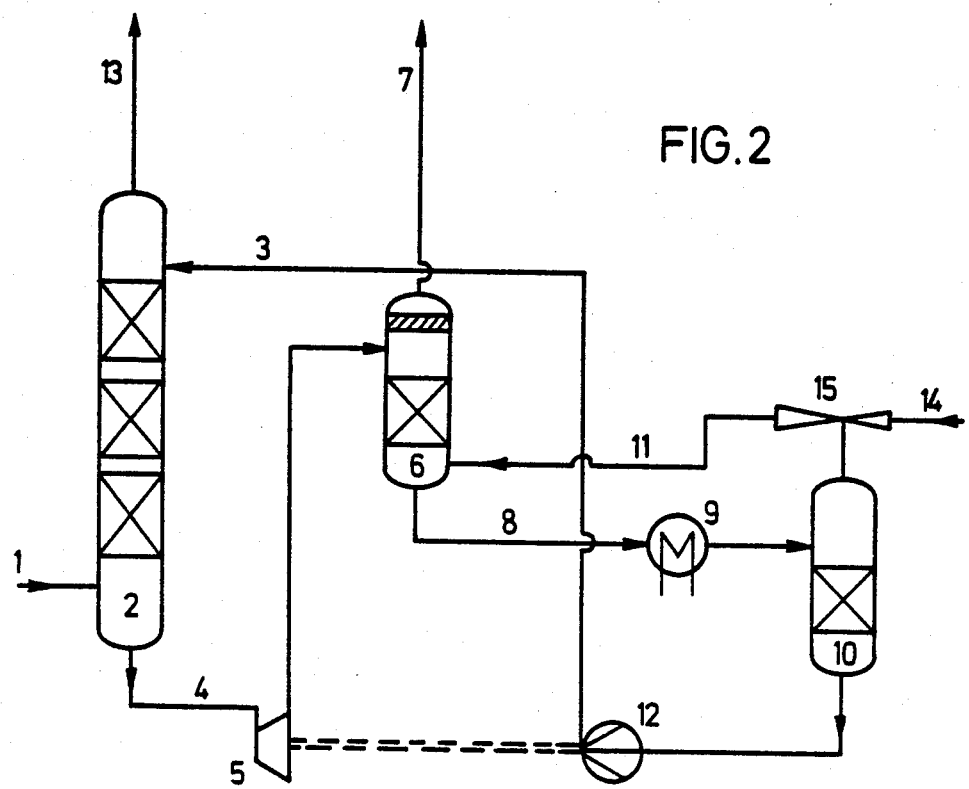

The two examples which follow illustrate the invention in more detail, the course of the process being shown diagrammatically in FIGS. 1 and 2.

In FIG. 1, a gas which contains $CO_2$ and/or $H_2S$, for example a natural as containing higher hydrocarbons, eg. aliphatic $C_2$–$C_{10}$-hydrocarbons, is passed under superatmospheric pressure, via line 1, into the bottom of absorption column 2. At the same time, an absorption liquid comprising from 20 to 70% strength by weight aqueous methyldiethanolamine solution is passed via line 3 to the top of the absorption column. The absorption liquid, which is fed counter-current to the gas, becomes laden with the acid gases $CO_2$ and/or $H_2S$, and the laden absorption liquid is taken off at the bottom of the absorpcolumn via line 4. The washed gas is taken off at the top of the absorption column via line 13. The stream of laden absorption liquid 4 is then let down in a flash chamber 6, for example via a valve or, preferably, an expansion turbine 5. In this stage, an intermediate flash gas containing hydrocarbons and $CO_2$ is liberated from the absorption liquid and is taken off at the top of flash chamber 6 via line 7. If necessary, steam, eg. low-pressure steam under 2.5 bar, is passed via line 14 into the bottom of flash chamber 6 in order to compensate the water losses in the system. At the bottom of flash chamber 6, the absorption liquid which has been partially let down is taken off via line 8 and heated in heat exchanger 9, for example by from 1° to 15° C., and the heated absorption liquid is let down in a second flash chamber 10 in which reduced pressure down to, for example, 0.5 bar is maintained, for example by means of vacuum pump 15. This liberates a $CO_2$-rich flash gas, for example having a $CO_2$ concentration of 98 mole %, and this gas is taken off at the top of flash chamber 10 via line 11. The regenerated absorption liquid taken off at the bottom of flash chamber 10 is recycled to the top of absorption column 2 with the aid of a circulatory pump 12.

In another example (cf. FIG. 2), the procedure described in the first example is followed except that, instead of a vacuum pump, steam-jet ejector 15 is used for producing reduced pressure in the second flash chamber 10; this ejector is supplied via line 14 with, for example, an amount of steam required to compensate the water losses in the system. The gas taken off at the top of flash chamber 10 is fed in, together with the steam used for operating the steam-jet ejector 15, at the bottom of the first flash chamber 6.

The Example which follows illustrates the invention.

EXAMPLE

The gas washer used comprises an absorption column and, downstream from this, three flash chambers in succession. In the absorption column, 3.15 kmol/hour of a $CO_2$-containing natural gas are washed, under 75 bar, with a 50% strength by weight aqueous methyldiethanolamine solution as the absorption liquid. The gas to be treated has the following composition:

| | |
|---|---|
| $CO_2$ | 10.0 mole % |
| $CH_4$ | 75.0 mole % |
| Higher hydrocarbons ($C_2$–$C_{12}$—hydrocarbons) | 15.0 mole %. |

The temperature of the absorption liquid in the feed to the absorption column is 70° C. The $CO_2$ content in the washed gas is less than 2 mole %. The laden wash liquid which leaves the absorption column is let down to 30 bar in a first flash chamber. In this procedure, 6.6 moles/hour of a hydrocarbon-rich intermediate flash gas having a $CO_2$ concentration of less than 10 mole % are liberated from the solution and taken off at the top of the first flash chamber. The partially let down absorption liquid is then heated in a heat exchanger, after which it is let down to 1.5 bar in a second flash chamber. In this procedure 0.13 kmol/hour of a $CO_2$-rich flash gas having a $CO_2$ concentration of more than 98 mole % is liberated and is taken off at the top of the second flash chamber.

The absorption liquid taken off at the bottom of the second flash chamber is passed through a heat exchanger, and then finally let down in a third flash chamber in which a pressure of 0.7 bar is maintained by means of a steam-jet ejector. The gas taken off at the top of the third flash chamber is passed, together with the steam used for operating the stated ejector, into the bottom of the second flash chamber. The absorption liquid taken off at the bottom of the third flash chamber is recycled to the top of the absorption column with the aid of a circulatory pump.

We claim:
1. A process for removing $CO_2$ and/or $H_2S$ from a gas containing $CO_2$ and/or $H_2S$, which comprises
   (a) treating said gas in an absorption stage at from 40° to 100° C. and at a pressure of from 10 to 110 bar with an aqueous absorption liquid containing from 20 to 70% by weight of methyldiethanolamine by feeding in the gas at the bottom and the aqueous absorption liquid at the top of the absorption stage, $CO_2$ and/or $H_2S$ being washed out by a counter-current procedure;
   (b) taking off the treated gas at the top of the absorption stage;
   (c) taking off the aqueous absorption liquid laden with $CO_2$ and/or $H_2S$ at the bottom of the absorption stage;
   (d) regenerating the laden aqueous absorption liquid without the use of a stripping column by flashing it in two or more flash stages, operating the final flash stage under a pressure of from 0.5 to about 1 bar; and
   (e) recycling the regenerated absorption liquid to the absorption stage.

2. The process of claim 1, wherein, to compensate water losses as a result of water being removed in the gas streams taken off at the top of the absorption stage and of the flash stages, an amount of steam corresponding to the water loss is fed in at the bottom of the penultimate flash stage.

3. The process of claim 1, wherein the reduced pressure in the final flash stage is obtained by means of the steam-jet ejector.

4. The process of claim 3, wherein the gas taken off at the top of the final flash stage is fed in, together with the steam used for operating the steam-jet ejector, at the bottom of the penultimate flash stage.

* * * * *